(12) United States Patent
Lin et al.

(10) Patent No.: US 10,208,093 B2
(45) Date of Patent: Feb. 19, 2019

(54) PLASMID, METHOD AND KIT THEREOF FOR PRODUCING HEAT LABILE ENTEROTOXIN B-SUBUNIT

(71) Applicant: AGRICULTURAL TECHNOLOGY RESEARCH INSTITUTE, Hsinchu (TW)

(72) Inventors: Jiunn-Horng Lin, Hsinchu (TW); Jyh-Perng Wang, Hsinchu (TW); Chien-Yu Fang, Hsinchu (TW); Zeng-Weng Chen, Hsinchu (TW); Ming-Wei Hsieh, Hsinchu (TW); Hao-Zhen Zeng, Hsinchu (TW); Jian-Fong Lai, Hsinchu (TW); Weng-Zeng Huang, Hsinchu (TW); Tzu-Ting Peng, Hsinchu (TW)

(73) Assignee: AGRICULTURAL TECHNOLOGY RESEARCH INSTITUTE, Hsinchu (TW)

( * ) Notice: Subject to any disclaimer, the term of this patent is extended or adjusted under 35 U.S.C. 154(b) by 305 days.

(21) Appl. No.: 15/104,105

(22) PCT Filed: Dec. 16, 2013

(86) PCT No.: PCT/CN2013/089559
§ 371 (c)(1),
(2) Date: Jun. 13, 2016

(87) PCT Pub. No.: WO2015/089707
PCT Pub. Date: Jun. 25, 2015

(65) Prior Publication Data
US 2017/0002045 A1    Jan. 5, 2017

(51) Int. Cl.
*C12N 1/20* (2006.01)
*C07K 14/245* (2006.01)
*C12N 15/75* (2006.01)

(52) U.S. Cl.
CPC .............. *C07K 14/245* (2013.01); *C12N 1/20* (2013.01); *C12N 15/75* (2013.01)

(58) Field of Classification Search
None
See application file for complete search history.

(56) References Cited

U.S. PATENT DOCUMENTS

| | | | |
|---|---|---|---|
| 4,411,888 A | 10/1983 | Klipstein et al. | |
| 5,589,384 A | 12/1996 | Lipscombe et al. | |
| 6,793,928 B1 | 9/2004 | Van Scharrenburg et al. | |
| 7,723,570 B2 * | 5/2010 | Piller ................. | A61K 39/0005 424/184.1 |
| 7,914,791 B1 | 3/2011 | Hirst et al. | |
| 2009/0035330 A1 | 2/2009 | Dewerchin | |
| 2010/0298419 A1 * | 11/2010 | Audonnet .............. | C12N 15/73 514/44 R |

OTHER PUBLICATIONS

Mauriello et al., Vaccine, 2004, vol. 22, pp. 1177-1187.*
Sim et al., Plant Mol Biol Rep, 2009, vol. 27, pp. 388-399.*
Amin et al., "Purification of the B-subunit Oligomer of *Escherichia coli* Heat-labile Enterotoxin by Heterologous Expression and Secretion in a Marine Vibrio," Protein Expression and Purification, vol. 5, 1994, 198-204.
Arimitsu et al., "Lincomycin-induced Over-expression of Mature Recombinant Cholera Toxin B Subunit and the Holotoxin in *Escherichia coli*," Protein Expression and Purification, vol. 67, 2009 (Available online May 3, 2009), pp. 96-103.
Cao et al., "Secretory Expression and Purification of Recombinant *Escherichia coli* Heat-labile Enterotoxin B Subunit and its Applications on Intranasal Vaccination of Hantavirus," Mol. Biotechnol., vol. 41, 2009 (Published online Dec. 17, 2008), pp. 91-98.
Fingerut et al., "Vaccine and Adjuvant Activity of Recombinant Subunit B of *E. coli* Enterotoxin Produced in Yeast," vol. 23, Vaccine, 2005 (Available online May 23, 2005), pp. 4685-4696.
Jeon et al., "Attenuated *Salmonella gailinarum* Secreting an *Escherichia coli* Heat-labile Enterotoxin B Subunit Protein as an Adjuvant for Oral Vaccination Against Fowl Typhoid," Veterinary Immunology and Immunopathology, vol. 150, 2012, pp. 149-160.
Kozuka et al., "Efficient Extracellular Production of Recombinant *Escherichia coli* Heat-labile Enterotoxin B Subunit by Using the Expression/secretion System of Bacillus Brevis and its Mucosal Immunoadjuvanticity," Vaccine, vol. 18, 2000, pp. 1730-1737.
Lim et al., "Expression of Functional Pentameric Heat-Labile Enterotoxin B Subunit of *Escherichia coli* in *Saccharomyces cerevisiae*," J. Microbiol. Biotechnol., vol. 19, No. 5, 2009 (Published online Jan. 13, 2009), pp. 502-510.
Loc et al., "Tissue Culture and Expression of *Escherichia coli* Heat-labile Enterotoxin B Subunit in Transgenic Peperomia Pellucida," Protein Expression and Purification, vol. 72, 2010 (Available online Feb. 20, 2010), pp. 82-86.
Loregian et al., "Use of *Vibrio* spp. for Expression of *Escherichia coli* Enterotoxin B Subunit Fusion Proteins: Purification and Characterization of a Chimera Containing a C-Terminal Fragment of DNA Polymerase from Herpes Simplex Virus Type 1," Protein Expr. Purif., vol. 8, No. 114, 1996, pp. 381-389.
Ma et al., "Comparative Study on Characterization of Recombinant B Subunit of *E. coli* Heat-labile Enterotoxin (rLTB) Prepared from *E. coli* and P. Pastoris," The Journal of Microbiology Biotechnol., vol. 20, No. 3, 2010 (Published online Feb. 6, 2010), pp. 550-557.

(Continued)

*Primary Examiner* — Mindy G Brown
(74) *Attorney, Agent, or Firm* — Birch, Stewart, Kolasch & Birch, LLP

(57) ABSTRACT

The present invention provides a plasmid, method and kit for producing heat labile enterotoxin B-subunit based on a *Bacillus subtilis* expression system. By comparing with the conventional method in the art, the present invention has the advantages of high safety, good yield, and simplified process and is therefore favorable for the commercialization object of heat labile enterotoxin B-subunit in the application of vaccine adjuvant.

Figure 2:
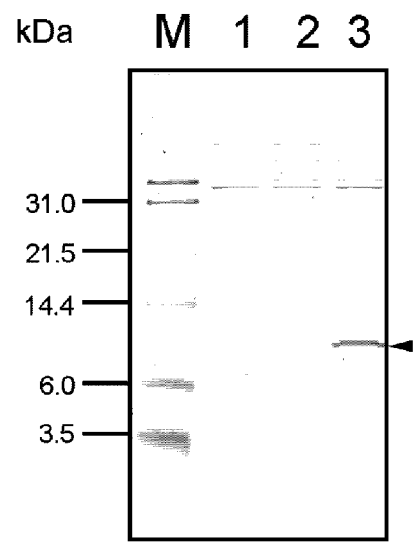
Figure 3:
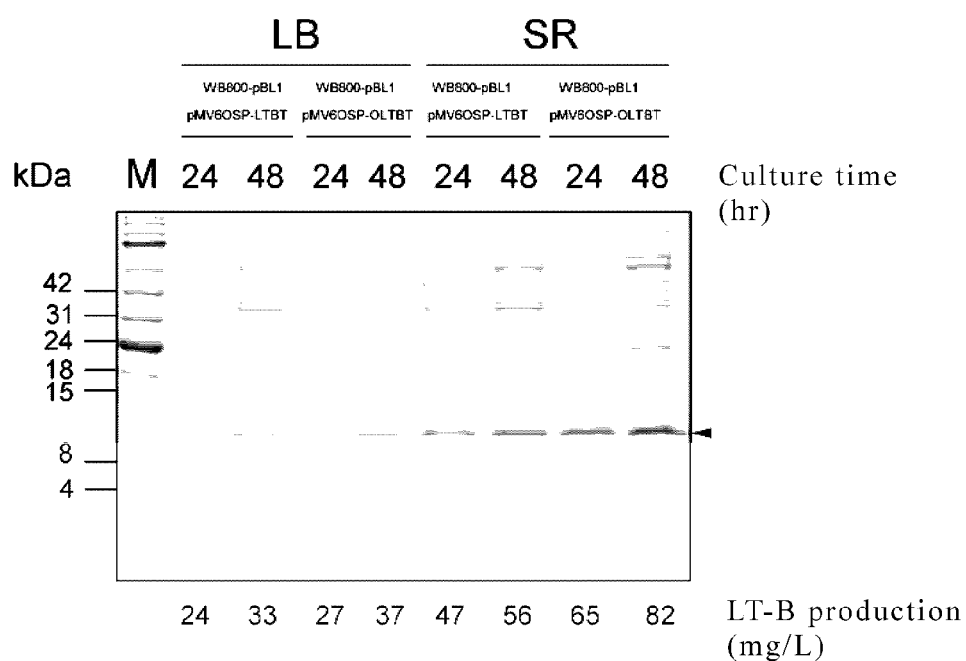
Figure 4:
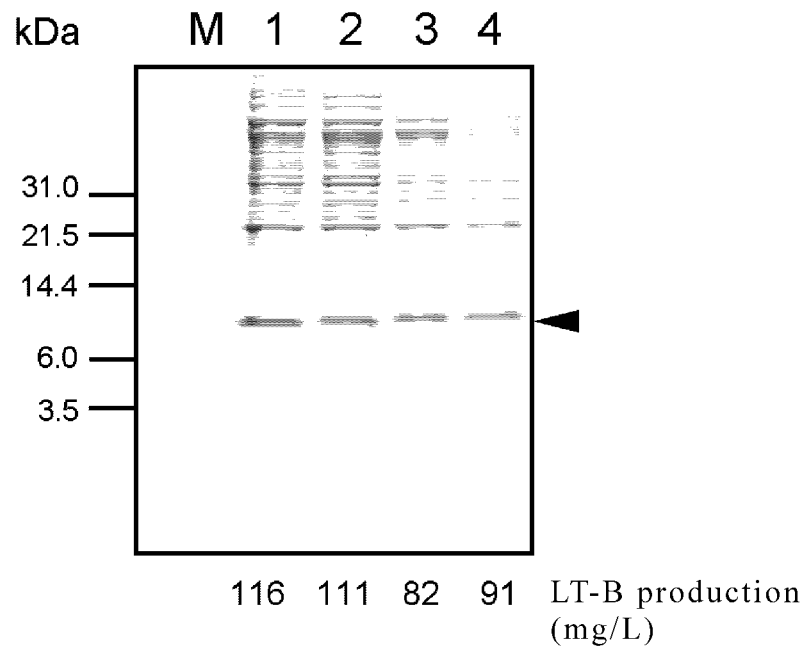
Figure 5:
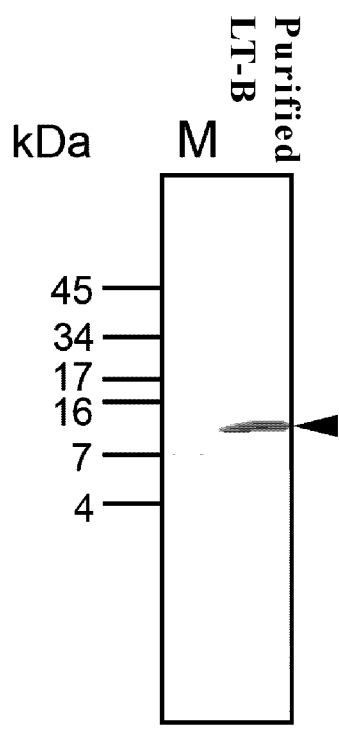

22 Claims, 4 Drawing Sheets
Specification includes a Sequence Listing.

(56) References Cited

OTHER PUBLICATIONS

Ma et al., "Construction of Bifidobacterium Infant's as a Live Oral Vaccine that Expresses Antigens of the Major Fimbrial Subunit (CfaB) and the B Subunit of Heat-labile Enterotoxin (LTB) from Enterotoxigenic *Escherichia coli*," Microbiology, vol. 158, 2012, pp. 498-504.

Ma et al., "Optimization and High-level Expression of a Functional GST-tagged rHLT-B in *Escherichia coli* and GM1 Binding Ability of Purified rHLT-B," The Journal of Microbiology, vol. 44, No. 3, Jun. 2006, pp. 293-300.

Mauriello et al., "Display of Heterologous Antigens on the Bacillus Subtilis Spore Coat Using CotC as a Fusion Partner," Vaccine, vol. 22, 2004, pp. 1177-1187.

Paccez et al., "Evaluation of Different Promoter Sequences and Antigen Sorting Signals on the Immunogenicity of Bacillus Subtilis Vaccine Vehicles," Vaccine, vol. 25, 2007 (Available online Apr. 25, 2007), pp. 4671-4680.

Paccez et al., "Stable Episomal Expression System Under Control of a Stress Inducible Promoter Enhances the Immunogenicity of Bacillus Subtilis as a Vector for Antigen Delivery," Vaccine, vol. 24, 2006 (Available online Dec. 27, 2005), pp. 2935-2943.

Soh et al., "Expression and Functional Validation of Heat-labile Enterotoxin B (LTB) and Cholera Toxin B (CTB) Subunits in Transgenic Rice (*Oryza sativa*)," SpringerPlus, vol. 4, 2015, pp. 1-14.

Wu et al., "Mice Protected by Oral Immunization with Lactobacillus Reuteri Secreting Fusion Protein of *Escherichia coli* Enterotoxin Subunit Protein," FEMS Immunol Med Microbiol, vol. 50, 2007 (Published online Jul. 27, 2007), pp. 354-365.

Yamamoto et al., "Sequence of Heat-labile Enterotoxin of *Escherichia coli* Pathogenic for Humans," Journal of Bacteriology, vol. 155, No. 2, Aug. 1983, pp. 728-733.

\* cited by examiner

Figure 1

```
                        SEQUENCE LISTING

<160> NUMBER OF SEQ ID NOS: 21

<210> SEQ ID NO 1
<211> LENGTH: 312
<212> TYPE: DNA
<213> ORGANISM: Escherichia coli

<400> SEQUENCE: 1
gcccctcaaa caatcacgga attatgctca gaatacagaa acacgcaaat ctacacaatc    60
aacgacaaaa tcttatccta cacagaatct atggcaggta aaagagaaat ggttatcatc   120
acatttaaat ccggcgaaac gtttcaagtt gaagtgccgg gatcacaaca tattgatagc   180
cagaaaaaag cgatcgaaag aatgaaagac acactgcgca ttacgtatct tacagaaacg   240
aaaatcgata aactgtgcgt ctggaacaac aaaacaccta actctatcgc tgctatctca   300
atgaaaaatt aa                                                        312

<210> SEQ ID NO 2
<211> LENGTH: 103
<212> TYPE: PRT
<213> ORGANISM: Escherichia coli

<400> SEQUENCE: 2

Ala Pro Gln Thr Ile Thr Glu Leu Cys Ser Glu Tyr Arg Asn Thr Gln
1               5                   10                  15

Ile Tyr Thr Ile Asn Asp Lys Ile Leu Ser Tyr Thr Glu Ser Met Ala
            20                  25                  30

Gly Lys Arg Glu Met Val Ile Ile Thr Phe Lys Ser Gly Glu Thr Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Thr Tyr Leu Thr Glu Thr
65                  70                  75                  80

Lys Ile Asp Lys Leu Cys Val Trp Asn Asn Lys Thr Pro Asn Ser Ile
                85                  90                  95

Ala Ala Ile Ser Met Lys Asn
            100

<210> SEQ ID NO 3
<211> LENGTH: 348
<212> TYPE: DNA
<213> ORGANISM: Artificial Sequence
<220> FEATURE:
<223> OTHER INFORMATION: PROMOTOR

<400> SEQUENCE: 3
gaattcagct cacacccgc atattgagga gtcatcatta ttcgcgaaca cattaagtcg    60
```

```
gcatgcacga caccatttat gatagatcct tgataaataa gaaaaacccc tgtataataa      120
aaaaagtgtg caaatcatgc acattttaaa taagtcttgc aacatgcgcc tattttctgt      180
ataatggtgt atgttggtca attgtgagcg gataacaatt gagctctttg actgcgatga      240
agtgagaggt tgctgacaca cccggccgct ttgccatggc aaggtgttca ggttttttctc     300 acggagaact gtctaacgtg atgtaggcga aaggaggga aacatatg                   348
```

```
<210> SEQ ID NO 4
<211> LENGTH: 171
<212> TYPE: DNA
<213> ORGANISM: Artificial Sequence
<220> FEATURE:
<223> OTHER INFORMATION: PROMOTOR

<400> SEQUENCE: 4
```

```
gaattccttg cggaacataa ttgaggaatc atagaatttt gtcaaaataa ttttattgac      60
aacgtcttat taacgttgat ataatttaaa ttttttttga caaaaatggg ctcgtgtggt     120
ataataaaaa ttgtgagcgg ataacaattt gtaaaaggag gaaaacatat g              171
```

```
<210> SEQ ID NO 5
<211> LENGTH: 87
<212> TYPE: DNA
<213> ORGANISM: Bacillus subtilis

<400> SEQUENCE: 5
```

```
atgaacatca aaagtttgc aaaacaagca acagtattaa cctttactac cgcactgctg      60
gcaggaggcg caactcaagc gtttgcg                                          87
```

```
<210> SEQ ID NO 6
<211> LENGTH: 38
<212> TYPE: DNA
<213> ORGANISM: Artificial Sequence
<220> FEATURE:
<223> OTHER INFORMATION: PRIMER

<400> SEQUENCE: 6
```

```
actagtcata tgtcgcgagg atccccccggg ctgcagat                             38
```

```
<210> SEQ ID NO 7
<211> LENGTH: 32
<212> TYPE: DNA
<213> ORGANISM: Artificial Sequence
<220> FEATURE:
<223> OTHER INFORMATION: PRIMER

<400> SEQUENCE: 7
```

```
atcgtcgaca tgcatctgca gcccggggga tc                                    32
```

```
<210> SEQ ID NO 8
<211> LENGTH: 48
<212> TYPE: DNA
<213> ORGANISM: Artificial Sequence
<220> FEATURE:
<223> OTHER INFORMATION: PRIMER

<400> SEQUENCE: 8
```

```
gatatagaat tcgctagcag atctactagt catatgtcgc gaggatcc                   48
```

```
<210> SEQ ID NO 9
<211> LENGTH: 55
<212> TYPE: DNA
<213> ORGANISM: Artificial Sequence
```

<220> FEATURE:
<223> OTHER INFORMATION: PRIMER

<400> SEQUENCE: 9
caatataagc tttacgtatc tagagcactc gagatcgtcg acatgcatct gcagc    55

<210> SEQ ID NO 10
<211> LENGTH: 35
<212> TYPE: DNA
<213> ORGANISM: Artificial Sequence
<220> FEATURE:
<223> OTHER INFORMATION: PRIMER

<400> SEQUENCE: 10
gttatacata tgaacatcaa aaagtttgca aaaca    35

<210> SEQ ID NO 11
<211> LENGTH: 59
<212> TYPE: DNA
<213> ORGANISM: Artificial Sequence
<220> FEATURE:
<223> OTHER INFORMATION: PRIMER

<400> SEQUENCE: 11
tagatagtcg acgcatgcgg atccagatct ggtaccttct ttcgcaaacg cttgagttg    59

<210> SEQ ID NO 12
<211> LENGTH: 41
<212> TYPE: DNA
<213> ORGANISM: Artificial Sequence
<220> FEATURE:
<223> OTHER INFORMATION: PRIMER

<400> SEQUENCE: 12
gttataggat ccgctcccca gactattaca gaactatgtt c    41

<210> SEQ ID NO 13
<211> LENGTH: 37
<212> TYPE: DNA
<213> ORGANISM: Artificial Sequence
<220> FEATURE:
<223> OTHER INFORMATION: PRIMER

<400> SEQUENCE: 13
tagatagtcg acctagtttt tcatactgat tgccgca    37

<210> SEQ ID NO 14
<211> LENGTH: 60
<212> TYPE: DNA
<213> ORGANISM: Artificial Sequence
<220> FEATURE:
<223> OTHER INFORMATION: PRIMER

<400> SEQUENCE: 14
gcccctcaaa caatcacgga attatgctca gaatacagaa acacgcaaat ctacacaatc    60

<210> SEQ ID NO 15
<211> LENGTH: 74
<212> TYPE: DNA
<213> ORGANISM: Artificial Sequence
<220> FEATURE:
<223> OTHER INFORMATION: PRIMER

<400> SEQUENCE: 15
ctcttttacc tgccatagat tctgtgtagg ataagatttt gtcgttgatt gtgtagattt    60

```
gcgtgtttct gtat                                                    74

<210> SEQ ID NO 16
<211> LENGTH: 70
<212> TYPE: DNA
<213> ORGANISM: Artificial Sequence
<220> FEATURE:
<223> OTHER INFORMATION: PRIMER

<400> SEQUENCE: 16
cacagaatct atggcaggta aaagagaaat ggttatcatc acatttaaat ccggcgaaac    60
gtttcaagtt                                                          70

<210> SEQ ID NO 17
<211> LENGTH: 79
<212> TYPE: DNA
<213> ORGANISM: Artificial Sequence
<220> FEATURE:
<223> OTHER INFORMATION: PRIMER

<400> SEQUENCE: 17
gtctttcatt ctttcgatcg cttttttctg gctatcaata tgttgtgatc ccggcacttc    60
aacttgaaac gtttcgccg                                                79

<210> SEQ ID NO 18
<211> LENGTH: 84
<212> TYPE: DNA
<213> ORGANISM: Artificial Sequence
<220> FEATURE:
<223> OTHER INFORMATION: PRIMER

<400> SEQUENCE: 18
aaagcgatcg aaagaatgaa agacacactg cgcattacgt atcttacaga aacgaaaatc    60
gataaactgt gcgtctggaa caac                                          84

<210> SEQ ID NO 19
<211> LENGTH: 63
<212> TYPE: DNA
<213> ORGANISM: Artificial Sequence
<220> FEATURE:
<223> OTHER INFORMATION: PRIMER

<400> SEQUENCE: 19
atttttcatt gagatagcag cgatagagtt aggtgttttg ttgttccaga cgcacagttt    60
atc                                                                 63

<210> SEQ ID NO 20
<211> LENGTH: 32
<212> TYPE: DNA
<213> ORGANISM: Artificial Sequence
<220> FEATURE:
<223> OTHER INFORMATION: PRIMER

<400> SEQUENCE: 20
caatatggat ccgcccctca aacaatcacg ga                                 32

<210> SEQ ID NO 21
<211> LENGTH: 43
<212> TYPE: DNA
```

-continued

```
<213> ORGANISM: Artificial Sequence
<220> FEATURE:
<223> OTHER INFORMATION: PRIMER

<400> SEQUENCE: 21
gatatagtcg acttaatttt tcattgagat agcagcgata gag                    43
```

PLASMID, METHOD AND KIT THEREOF FOR PRODUCING HEAT LABILE ENTEROTOXIN B-SUBUNIT

BACKGROUND

Technical Field

The present invention is related to a method for producing heat labile enterotoxin B-subunit; especially a method for producing heat labile enterotoxin B-subunit by using *Bacillus subtilis*.

Description of Related Art

*Escherichia coli* heat labile enterotoxin (LT) is a kind of exotoxin released by enterotoxingenic *E. coli* composed of one subunit A (LT-A) and five subunit B (LT-B). LT-A is mainly the source of toxin comprising activity of ADP-ribosyltransferase, which actives adenylate cyclase while entering cells of small intestine, causes cAMP accumulation and thereby actives protein kinase A. Consequently, $Na^+$, $K^+$, and water in the cells would transfer into the cavity of the intestine and cause diarrhea, dehydration, and electrolyte disturbance. LT-B serves to bind to the GM1 ganglioside receptor on the cell membrane of intestine cells and assists LT-A entering cells.

Studies have shown LT, LT-A, and LT-B all have effects in immune response regulation and are suitable to be used as mucosal adjuvant. Among them, LT-B has no toxicity and therefore is particularly suitable to be used as adjuvant for stimulating immune response. Although the adjuvant role of LT-B has been taught, it remains critical of how to mass produce LT-B for the need of the industry. The field commonly uses *Escherichia coli*, *Brevibacillus choshinensis*, *Saccharomyces cerevisiae*, and *Pichia pastoris* for producing recombinant LT-B, which is then used as adjuvant. However, the conventional expression systems all have its drawbacks. Cases in point: (1) the *E. coli* system has advantage of ease-in-operation. However, recombinant LT-B was expressed mainly as insoluble inclusion bodies in *E. coli*. This situation causes increase in the LT-B production cost (Ma et al., 2010). Moreover, *E. coli* has endotoxin; that said, the endotoxin has to be removed from the purified LT-B to ensure the safety of applying the produced recombinant LT-B in human or pet vaccines. (2) The *B. choshinensis* system is able to secrete the recombinant protein out of the cells; however, it takes 8 days culture at 30° C. to achieve the largest production (350 mg/L). That said, it has a longer production period. (Kozuka et al., 2000) (3) The *S. cerevisiae* system is generally recognized as safe (GRAS) and is also able to secrete the recombinant protein out of the cells. However, the production thereof is too low (about 3 mg/L) (Lim et al., 2009). (4) The *Pichia pastoris* system is able to secrete the recombinant protein out of the cells and has reliable production (Ma et al., 2010). However, the expression system requires methanol as inducer, which is highly concerned from the perspective of industrial management, usage safety and etc.

To sum up, the conventional methods used for producing *Escherichia coli* heat labile enterotoxin B-subunit in the field have spaces for improvement. In order to fulfill the promising effects of *Escherichia coli* heat labile enterotoxin B-subunit in being used as adjuvant, the field needs a production method of ease-in-operation, good production, and reliable safety.

SUMMARY

In light of the foregoing, one of the objectives of the present invention is to provide a plasmid for producing *Escherichia coli* heat labile enterotoxin B-subunit and kit containing the same; wherein said kit has the advantage of high safety and is particularly suitable for human or animal vaccines.

Another objective of the present invention is to provide a method for producing *Escherichia coli* heat labile enterotoxin B-subunit, which adapts an expression system of simpler production procedure and therefore reduces the production costs.

In order to achieve the aforesaid objectives, the present invention provides a plasmid for producing *Escherichia coli* heat labile enterotoxin B-subunit, comprising: a nucleotide sequence encoding *Escherichia coli* heat labile enterotoxin B-subunit; and an expression element recognizable by *Bacillus subtilis*.

Preferably, said plasmid is used in a *Bacillus subtilis* expression system.

Preferably, said nucleotide sequence encoding *Escherichia coli* heat labile enterotoxin B-subunit has a sequence of SEQ ID NO: 01.

Preferably, said *Escherichia coli* heat labile enterotoxin B-subunit has an amino acid sequence of SEQ ID NO: 02.

Preferably, said expression element recognizable by *Bacillus subtilis* is P43 expression element, veg expression element, trc expression element, lacuv5 expression element, SPO1 expression element, P59 expression element, PS10 expression element, rpsF expression element, ytkA expression element, ywoF expression element, ldh expression element, nap expression element, HpaII expression element, PΦ105 expression element, PR expression element, des expression element, xylA expression element, T7 expression element, groE-gntO expression element, glv expression element, araA expression element, nisA expression element, spaS expression element, pst expression element, vanH expression element, gsiB expression element, amy expression element, citM expression element, gcv-riboswitch region expression element, acoA expression element, tac-lacO expression element, T5-lacO expression element, spac expression element, sacB expression element, rpsJ-lacO expression element, veg6-lacO expression element, or a combination thereof.

Preferably, said rpsJ-lacO expression element has a nucleotide sequence of SEQ ID NO: 03.

Preferably, said veg6-lacO expression element has a nucleotide sequence of SEQ ID NO: 04.

Preferably, said plasmid further comprises a nucleotide sequence encoding a signal peptide of a secretory protein.

Preferably, said signal peptide is a signal peptide of levansucrase.

Preferably, said signal peptide of levansucrase has a nucleotide sequence of SEQ ID NO: 05.

The present invention also provides a method for producing *Escherichia coli* heat labile enterotoxin B-subunit, comprising expressing said plasmid of claim 1 in a *Bacillus subtilis* expression system.

Preferably, said nucleotide sequence encoding *Escherichia coli* heat labile enterotoxin B-subunit of said plasmid has a sequence of SEQ ID NO: 01.

Preferably, said plasmid further comprises a nucleotide sequence encoding a signal peptide of a secretory protein.

Preferably, said method comprises the following steps: (A) culturing a strain of *Bacillus subtilis* transformed with said plasmid in a culture medium; (B) inducing the expression of said nucleotide sequence encoding *Escherichia coli* heat labile enterotoxin B-subunit of said plasmid; and (C) collecting said culture medium and obtaining said *Escherichia coli* heat labile enterotoxin B-subunit via purification.

Preferably, said culture medium is LB medium, SR medium, or a combination thereof.

Preferably, said strain of *Bacillus subtilis* expresses LacI, and said expression element recognizable by *Bacillus subtilis* of said plasmid is rpsJ-lacO expression element or veg6-lacO expression element; said inducing of said step (B) is achieved by adding allolactose, isopropyl β-D-thiogalactopyranoside, or alike thereof.

Preferably, said step (B) is not conducted until said culturing of said step (A) achieves an $OD_{600}$ of 0.3 to 0.5.

Preferably, said purification is achieved by introducing said culture medium through an immobilized galactose resin column.

Preferably, a production of said *Escherichia coli* heat labile enterotoxin B-subunit is 100 mg/L to 200 mg/L based on a total volume of said culture medium of said step (C)

Preferably, said culturing of said step (A) is continuous for 24 to 72 hours.

Preferably, said culture of said step (A) contains 0.1 wt % to 0.8 wt % of glucose based on a total weight of said culture medium of said step (A).

The present invention more provides a kit for producing *Escherichia coli* heat labile enterotoxin B-subunit, comprising: a strain of *Bacillus subtilis* transformed with said plasmid of claim 1.

Preferably, said expression element recognizable by *Bacillus subtilis* is rpsJ-lacO expression element or veg6-lacO expression element and said *Bacillus subtilis* expresses LacI.

Preferably, said kit further comprises a reagent for inducing the expression of said plasmid.

Preferably, said reagent is allolactose, isopropyl β-D-thiogalactopyranoside, or alike thereof.

To sum up, the present invention relates to a plasmid for producing *Escherichia coli* heat labile enterotoxin B-subunit, a kit containing the same, and a method for producing *Escherichia coli* heat labile enterotoxin B-subunit by using said plasmid. The present invention succeeded in establishing a *Bacillus subtilis* expression system for producing recombinant heat labile enterotoxin B-subunit. The present method has advantages of good yield rate and ease-to-operation; therefore is more advanced than the conventional methods in the field.

BRIEF DESCRIPTION OF THE DRAWINGS

Figure 1:
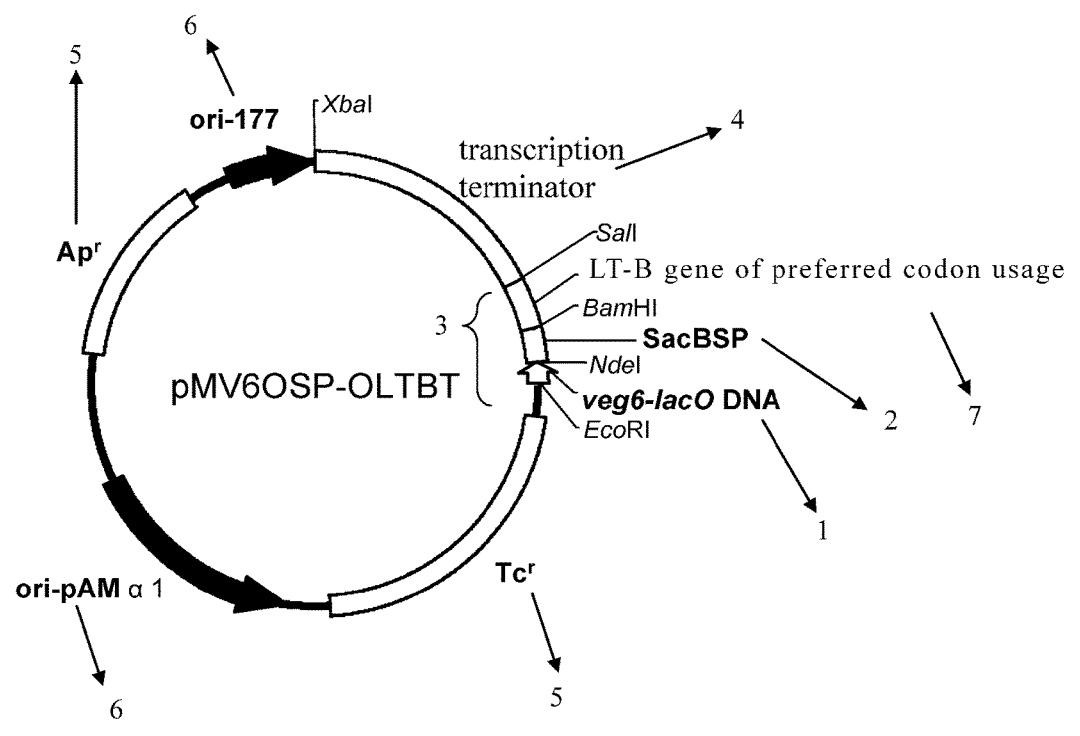

FIG. 1 illustrates the present plasmid pMV6OSP-OLTBT.

FIG. 2 compares the LT-B production of *Bacillus subtilis* having pBL1 and pMCST (Lane 1), *Bacillus subtilis* having pBL1 and pMROSP-LTBT (Lane 2), and *Bacillus subtilis* having pBL1 and pMV6OSP-LTBT (Lane 3). M stands for Mark12™ Protein Standard (Invitrogen, USA).

FIG. 3 shows the change of LT-B production in different culture medium and different culture time; wherein both of the *Bacillus subtilis* having pBL1 and pMV6OSP-OLTBT and *Bacillus subtilis* having pBL1 and pMV6OSP-LTBT were used in these experiments. M stands for Mark12™ Protein Standard (Invitrogen, USA).

FIG. 4 shows the change of LT-B production in cultures of different glucose concentrations. The experiments result shown in this figure were collected by culturing *Bacillus subtilis* (*Bacillus subtilis* WB800; pBL1, pMV6OSP-OLTBT) in SR culture mediums of different glucose concentrations respectively and culturing the same under induction for 72 hours; wherein lane 1 shows a SR medium of 0.1 wt % glucose; lane 2 shows a SR medium of 0.2 wt % glucose; lane 3 shows a SR medium of 0.4 wt % glucose; lane 4 shows a SR medium of 0.6 wt % glucose. M stands for Mark12™ Protein Standard (Invitrogen, USA).

FIG. 5 shows the purification efficiency of LT-B of the Example 2 of the present invention. M stands for Mark12™ Protein Standard (Invitrogen, USA).

FIG. 6 shows the evaluation of the adjuvant effect of LT-B in female BALB/c mice.

DETAILED DESCRIPTION

Prokaryotic expression system is a kind of tools for genetic engineering. The field to which the present invention pertains has known several bacteria suitable for construction of expression systems. Nevertheless, the efficiency of producing any particular protein in any known expression system is not always foreseeable. Case in point, although the field has known several expression systems for producing *Escherichia coli* heat labile enterotoxin B-subunit, each of them shall have its pros and cons, and moreover, some of them can only provide undesirable low production rate. That said, even the field has already been familiar with the basic knowledge of prokaryotic expression system, it still requires certain amounts of trials and modification for practically producing some particular proteins while the production efficiency is completely not foreseeable before then.

One of the contributions of the present invention is success in establishing a novel *Bacillus subtilis* expression system for producing recombinant heat labile enterotoxin B-subunit. *Bacillus subtilis* is a gram-positive, facultative anaerobic, spore-forming, rod-shaped bacterium. Like *S. cerevisiae, Bacillus subtilis* is also a GRAS bacteria; whereas, unlike the low production of *S. cerevisiae* system, the present *Bacillus subtilis* expression system is able to produce 100 mg/L to 200 mg/L of *Escherichia coli* heat labile enterotoxin B-subunit. In other words, the present invention has both the advantages of safety and good production. In an embodiment of the present invention, the present invention succeeds in producing *Escherichia coli* heat labile enterotoxin B-subunit as secreted protein, which is favorable for purifying the produced protein and therefore reducing the steps and costs for production.

Generally, a plasmid used for expression systems contains, other than the gene to be expressed, (1) expression element, (2) signal peptide DNA, (3) restriction enzyme cutting site(s), (4) transcription terminator, (5) selection marker, and/or (6) origin of replication. Said expression element has sequences for transcription and translation, which are necessary for gene expression. Said signal peptide is a secretion signal required for protein translocation. Said restriction enzyme cutting site(s) is convenient for DNA cloning. Said transcription terminator, located at the downstream of the gene to be expressed, is for stopping the transcription. According to the researches, transcription terminator is able to improve the stability of mRNA and prevent from transcription readthrough and instability of the plasmid. Said selection marker is used for selecting the transformed strains. Drug resistance gene is usually used as said selection marker. Said origin of replication is used for starting the replication of the plasmid in host cells.

In an aspect, the present invention provides a plasmid for producing *Escherichia coli* heat labile enterotoxin B-subunit, comprising a nucleotide sequence encoding *Escherichia coli* heat labile enterotoxin B-subunit; and an expression element recognizable by *Bacillus subtilis*. In an alternative embodiment, said nucleotide sequence encoding *Escherichia coli* heat labile enterotoxin B-subunit can be inferred based on the codon usage of *Bacillus subtilis* from the well-known amino acid sequence of *Escherichia coli* heat labile enterotoxin B-subunit (for instance but not limited to SEQ ID NO: 02). In an alternative embodiment, said nucleotide sequence encoding *Escherichia coli* heat labile enterotoxin B-subunit is as shown in SEQ ID NO: 01.

In a preferable embodiment, said expression element recognizable by *Bacillus subtilis* is a constitutive-type expression element, which is favorable for continuously expressing the desired gene, or an inducible-type expression element, which is favorable for controlling the start and stop of the system. Usable constitutive-type expression element includes but not limited to P43 expression element, veg expression element, trc expression element, lacuv5 expression element, SPO1 expression element, P59 expression element, PS10 expression element, rpsF expression element, ytkA expression element, ywoF expression element, ldh expression element, nap expression element, HpaII expression element, or a combination thereof. ο Usable inducible-type expression element includes but not limited to PΦ105 expression element, PR expression element, des expression element, xylA expression element, T7 expression element, groE-gntO expression element, glv expression element, araA expression element, nisA expression element, spaS expression element, pst expression element, vanH expression element, gsiB expression element, amy expression element, citM expression element, gcv-riboswitch region expression element, acoA expression element, tac-lacO expression element, T5-lacO expression element, spac expression element, sacB expression element, rpsJ-lacO expression element, veg6-lacO expression element, a combination thereof.

In a preferable embodiment, said expression element recognizable by *Bacillus subtilis* is rpsJ-lacO expression element or veg6-lacO expression element. When rpsJ-lacO expression element or veg6-lacO expression element is used as said expression element, it can be used with a *Bacillus subtilis* strain expressing lactose repressor. Through this way, one can control the operation of the system by adding allolactose, isopropyl β-D-thiogalactopyranoside, or alike thereof for inducing the onset of said expression element. Preferably, said rpsJ-lacO expression element has a nucleotide sequence as SEQ ID NO: 03. Preferably, said veg6-lacO expression element has a nucleotide sequence as SEQ ID NO: 04.

In the mechanism of using allolactose or isopropyl β-D-thiogalactopyranoside for inducing the onset of rpsJ-lacO or veg6-lacO expression element, allolactose or isopropyl β-D-thiogalactopyranoside would bind to said Lac repressor (LacI) and restrain the repression activity thereof and thereby induce the activation of said rpsJ-lacO or veg6-lacO expression element. Accordingly, the term of "alike thereof" of said "allolactose, Isopropyl β-D-thiogalactopyranoside, or alike thereof" refers to a substance, which has a structure similar with the structure of said allolactose or said isopropyl β-D-thiogalactopyranoside for binding with said lactose repressor. Thus, said substance is able to imitate the binding condition between said allolactose and said lactose repressor, said isopropyl β-D-thiogalactopyranoside and said lactose repressor and thereby results in the effect of restraining the activity of said lactose repressor.

In a preferable embodiment, said plasmid further comprises a nucleotide sequence encoding a signal peptide of a secretory protein. Said signal peptide is to recognized by *Bacillus subtilis*, and the *Bacillus subtilis* would actively secrete the *Escherichia coli* heat labile enterotoxin B-subunit out of the cells. This feature is favorable for collecting the produced *Escherichia coli* heat labile enterotoxin B-subunit from the culture supernatant so that the production procedures can be simplified and costs thereof can be reduced. Preferably, said signal peptide is the signal peptide of levansucrase. More preferably, said signal peptide of levansucrase has a nucleotide sequence as SEQ ID NO: 05.

In another aspect, the present invention provides a method for producing *Escherichia coli* heat labile enterotoxin B-subunit, comprising expressing said plasmid in a *Bacillus subtilis* expression system. Preferably, said method comprises the following steps: (A) culturing a *Bacillus subtilis* strain transformed with said plasmid in a culture medium; (B) inducing expression of said nucleotide sequence encoding *Escherichia coli* heat labile enterotoxin B-subunit of said plasmid; and (C) collecting said culture supernatant and obtaining said *Escherichia coli* heat labile enterotoxin B-subunit through purification.

In an alternative embodiment, conventional transformation manners can be adopted for transforming the present plasmid into a *Bacillus subtilis* strain. Preferably, said plasmid may further comprise a selection marker for selecting whether or not the transformation procedure is success. For instance, said selection marker may be a drug resistance gene or may adopt the concept of Blue and White Screening common in the field. Said culture medium may be, but not limited to LB medium, SR medium, or a combination thereof. Said LB medium or said SR medium are prepared according to the conventional formulation in the field. However, those having ordinary skill in the art can adjust the formulation based on its need but the adjusted formulation is still within the scope of the present invention. Nevertheless, the researches of the present invention showed a preferable culture environment is a SR medium comprising 0.1 to 0.8 wt %. A SR medium comprising 0.1 wt % is even preferable. In a preferable embodiment, said culture is conducted for 24 to 72 hours.

In a preferable embodiment, said *Bacillus subtilis* strain expresses Lac suppressor (LacI) and said expression element recognizable by *Bacillus subtilis* in said plasmid is rpsJ-lacO expression element or veg6-lacO expression element. Accordingly, said expression element can be induced for expression by adding allolactose, isopropyl β-D-thiogalactopyranoside, or alike thereof (step (B)).

In a preferable embodiment, said step (B) is not conduct until said culture of *Bacillus subtilis* strain reaches an $OD_{600}$ value of 0.3 to 0.5. The aforesaid condition is set to gradually adapt said *Bacillus subtilis* strain with the environment for *Escherichia coli* heat labile enterotoxin B-subunit production, which is favorable for stabilize the whole expression system.

In an alternative embodiment, a centrifugation step can be conducted after the culture medium is collected for precipitating the impurity therein. The centrifugation step is favorable for improving the efficiency of the subsequent purification step. In a preferable embodiment, said purification may be conducted by taking advantage of the binding property of *Escherichia coli* heat labile enterotoxin B-subunit with galactose; wherein said culture medium is introduced an immobilized galactose resin column and the produced *Escherichia coli* heat labile enterotoxin B-subunit would be selectively captured in the column. After that, an elution buffer is introduced into said resin column to elute the captured *Escherichia coli* heat labile enterotoxin B-subunit.

In another aspect, the present invention provides a kit for producing *Escherichia coli* heat labile enterotoxin B-subunit, comprising a *Bacillus subtilis* strain transformed with said plasmid. Preferable, said kit further comprises a reagent for inducing the expression of said plasmid. Said reagent may be allolactose, isopropyl β-D-thiogalactopyranoside, or alike thereof; wherein said alike is defined as set forth in the previous paragraphs.

The following examples recite the trials and experiments conducted during the development of the present invention for further explaining the features and advantages of the present invention. Nevertheless, the following examples are merely exemplary for clarifying the present invention and shall not be used for limiting the claim scope of the present invention.

Example 1: Strains and Culture Thereof

In the development of the present invention, *Escherichia coli* TA-196ELT was used as the source of LT-B gene and *Escherichia coli* JM109 was used as the host cell for gene cloning. Besides, *Bacillus subtilis* WB800 (pBL1) was used as the host cell for protein expression.

Said *Escherichia coli* strain was cultured in LB medium (Luria-Bertani, Difco, USA). Said *Bacillus subtilis* strain was cultured in LB medium or SR medium (2% yeast extract, 2.5% Bacto tryptose, 0.3% $K_2HPO_4$, pH 7.5).

Example 2: Construction of the Plasmid of the Present Invention

1. Construction of p300MCST

In order to facilitate the subsequence cloning steps, this experiment replaced the original multiple cloning site of plasmid pHY300PLK (Takara, Japan) with an artificial multiple cloning site.

First of all, the synthesis of the multiple cloning site was made by using overlapping-extension polymerase chain reaction, OEPCR; wherein the restriction enzyme cutting sites set therein included EcoRI, BglII, SpeI, NdeI, NruI, BamHI, XmaI, PstI, SalI, XhoI, XbaI, and HindIII. The primers designed for use included MCST1, MCST2, MCSF, and MCSR (See Table 1); wherein MCST1 and MCST2 were used as template primers while MCSF and MCSR are used as amplification primers.

TABLE 1

| Name | Sequence (5' to 3') | SEQ ID NO: |
|---|---|---|
| MCST1 | ACTAGTCATATGTCGCGAGGATCCCCCGGGCTGCAGAT | 06 |
| MCST2 | ATCGTCGACATGCATCTGCAGCCCGGGGGATC | 07 |
| MCSF | GATATAGAATTCGCTAGCAGATCTACTAGTCATATGTCGCGAGGATCC | 08 |
| MCSR | CAATATAAGCTTTACGTATCTAGAGCACTCGAGATCGTCGACATGCATCTGCAGC | 09 |

The template primers would anneal together during the PCR reaction while the DNA polymerase would recognized the 3'-5' primer as template and elongate from the 5'-3' primer to produce a full length DNA. Then, the amplification primers used the full length DNA as template and massively amplified the desired DNA fragments. The PCR mixture (50 μL) comprised 1×GDP-HiFi PCR buffer B, 200 μM of dNTP (dATP, dTTP, dGTP, and dCTP), 1 μM of primer, and 1 U GDP-HiFi DNA polymerase. The PCR condition was one cycle of 98° C. for 2 minutes, 35 cycles of 94° C. for 30 seconds, 55° C. for 30 seconds, and 68° C. for 30 seconds, one cycle of 68° C. for 5 minutes. After the PCR reaction, the PCR product was checked by electrophoresis to see if there was any DNA fragment of expected size. Then a PCR-M™ Clean Up system kit (GeneMark, Taiwan) was used for collecting the PCR product in the gel. Afterwards, the collected PCR product was cut by EcoRI and HindIII and ligated into pHY300PLK cut by the same restriction enzymes. The resulting ligation product was transformed in to *Escherichia coli* ECOS 9-5. Colony PCR was conducted to screen strains of success transformation; wherein DNA electrophoresis was conducted to confirm the recombinant plasmid did have the insert DNA. Then the plasmid was isolated for DNA sequencing. The plasmid confirmed to have the correct insert DNA via DNA sequencing was named p300MCS.

Afterward, plasmid pQE30 (Qiagen, USA) was cut by SalI and XbaI and the DNA fragment of smaller molecular weight was collected. This fragment contained Lambda t0 terminator and rrnB T1 terminator. This fragment was then ligated into p300MCS cut by the same restriction enzymes. The resulting ligation product was transformed into *Escherichia coli* ECOS 9-5 via electroporation. The transformed strains were randomly picked and the plasmids thereof were isolated and cut by restriction enzyme. The plasmid of correct molecular size was named p300MCST.

2. Construction of Expression Vector:

One of the objectives of the present invention is to establish an expression system for exogenous gene expression for producing *Escherichia coli* heat labile enterotoxin B-subunit. In order to use *Bacillus subtilis* as host cells for exogenous gene expression, the upstream of the desired exogenous gene shall contain an expression element recognizable by *Bacillus subtilis*, including signal for transcription and translation, for achieving the purpose of gene expression.

This example respectively used rpsJ-lacO expression element and veg6-lacO expression element for plasmid construction. Said rpsJ-lacO expression element is derived from rpsJ gene of *Bacillus subtilis* by inserting lacO sequence from *Escherichia coli* lac operon into the −10 region of the rpsJ gene. Said veg6-lacO expression element is derived from veg6 gene of *Bacillus subtilis* by replacing the TACAAT of −10 region thereof with TATAAT, inserting a TG motif into the −16 region, inserting lacO sequence into the −10 region, shortening the distance between the −10 region and the −35 region from 17 bp to 16 bp, and replacing AGTGAGGTG of SD sequence with AAAGGAGG. Accordingly, the aforesaid expression elements respectively have sequences as shown in SEQ ID NO: 03 and SEQ ID NO: 04.

The aforesaid expression element was cut by EcoRI and NdeI, and the resulted DNA fragment was ligated into p300MCST cut by the same restriction enzymes by DNA ligase. The resulting ligation product was then transformed in to *Escherichia coli* ECOS 9-5. The transformed strains were screened by colony PCR. After checking the recombinant plasmid did have the insert DNA, the plasmids of the transformed strains were isolated for DNA sequencing. Plasmids being checked to have the correct insert DNA by DNA sequencing were named p300MROT and p300MV6OT respectively.

3. Construction of Secretion Protein Expression Vector:

The chromosome of *Bacillus subtilis* was used as template. Primer set of SacBSPF (5'-GTTATACATAT-GAACATCAAAAAGTTTGCAAA ACA-3'; SEQ ID NO:

10)/SacBSPR (5'-TAGATAGTCGA CGCATGCGGATC-CAGATCTGGTACCTTCTTTCGCAAACGCTT-GAGTTG-3'; SEQ ID NO: 11) was used for amplifying the DNA fragment encoding levansucrase signal peptide (SacBSP).

The PCR mixture (50 μL) comprised 1×GDP-HiFi PCR buffer B, 200 μM of dNTP (dATP, dTTP, dGTP, and dCTP), 1 μM of amplification primer, 200 ng of *Bacillus subtilis* chromosome, and 1 U GDP-HiFi DNA polymerase. The PCR condition was one cycle of 98° C. for 5 minutes, 35 cycles of 94° C. for 30 seconds, 55° C. for 30 seconds, and 68° C. for 45 seconds, one cycle of 68° C. for 5 minutes. After the PCR reaction, the PCR product was checked by electrophoresis to see if there was any DNA fragment of expected size. Then a PCR-M™ Clean Up system kit (GeneMark, Taiwan) was used for collecting the PCR product in the gel. Afterwards, the collected PCR product was cut by NdeI and SalI and, the resulted DNA fragment was ligated into p300MROT or p300MV6OT cut by the same restriction enzymes. The resulting ligation product was transformed into *Escherichia coli* ECOS 9-5. Colony PCR was conducted to screen strains of success transformation; wherein DNA electrophoresis was conducted to confirm the recombinant plasmid did have the insert DNA. Then the plasmid was isolated for DNA sequencing. The plasmid confirmed to have the correct insert DNA via DNA sequencing was named pMROSPT or pMV6OSPT respectively.

4. Construction of Secretion LT-B Expression Vector:

TA-196ELT was used as template and a primer set of LTBF (5'-GTTATAGGATCCGCTCCCCAGACTATTACA-GAACTATGTTC-3'; SEQ ID NO: 12)/LTBR (5'-TAGA-TAGTCGACCTAG TTTTTCATACTGATTGCCGCA-3'; SEQ ID NO: 13) was used for LT-B gene amplification.

The PCR mixture (50 μL) comprised 1×GDP-HiFi PCR buffer B, 200 μM of dNTP (dATP, dTTP, dGTP, and dCTP), 1 μM of amplification primer, 200 ng of TA-196ELT, and 1 U GDP-HiFi DNA polymerase. The PCR condition was one cycle of 98° C. for 5 minutes, 35 cycles of 94° C. for 30 seconds, 55° C. for 30 seconds, and 68° C. for 30 seconds, one cycle of 68° C. for 5 minutes. After the PCR reaction, the PCR product was checked by electrophoresis to see if there was any DNA fragment of expected size. Then a PCR-M™ Clean Up system kit (GeneMark, Taiwan) was used for collecting the PCR product in the gel. Afterwards, the collected PCR product was cut by BamHI and SalI and, the resulted DNA fragment was ligated into pMROSPT or pMV6OSPT cut by the same restriction enzymes. The resulting ligation product was transformed into *Escherichia coli* ECOS 9-5. Colony PCR was conducted to screen strains of success transformation; wherein DNA electrophoresis was conducted to confirm the recombinant plasmid did have the insert DNA. Then the plasmid was isolated for DNA sequencing. The plasmid confirmed to have the correct insert DNA via DNA sequencing was named pMROSP-LTBT or pMV6OSP-LTBT respectively.

5. Modification of Secretion LT-B Expression Vector:

According to the preferred codons usage of *Bacillus subtilis*, the amino acid sequence of LT-B (ex. as shown in SEQ ID NO: 02) was reversely derived into nucleotide sequence (ex. as shown in SEQ IN NO: 01). Primers OLTB-T1, OLTB-T2, OLTB-T3, OLTB-T4, OLTB-T5, OLTB-T6, OLTBF, and OLTBR were designed based on the nucleotide sequence and were listed in the following Table 2.

Table 2

| Name | Sequence (5' to 3') | SEQ ID NO: |
|---|---|---|
| OLTB-T1 | GCCCCTCAAACAATCACGGAATTATGCTCAGAATACAGAAACACGCAAATCTACACAATC | 14 |
| OLTB-T2 | CTCTTTTACCTGCCATAGATTCTGTGTAGGATAAGATTTTGTCGTTGATTGTGTAGATTTGCGTGTTTCTGTAT | 15 |
| OLTB-T3 | CACAGAATCTATGGCAGGTAAAAGAGAAATGGTTATCATCACATTTAAATCCGGCGAAACGTTTCAAGTT | 16 |
| OLTB-T4 | GTCTTTCATTCTTTCGATCGCTTTTTTCTGGCTATCAATATGTTGTGATCCCGGCACTTCAACTTGAAACGTTTCGCCG | 17 |
| OLTB-T5 | AAAGCGATCGAAAGAATGAAAGACACACTGCGCATTACGTATCTTACAGAAACGAAAATCGATAAACTGTGCGTCTGGAACAAC | 18 |
| OLTB-T6 | ATTTTTCATTGAGATAGCAGCGATAGAGTTAGGTGTTTTGTTGTTCCAGACGCACAGTTTATC | 19 |
| OLTBF | CAATATGGATCCGCCCCTCAAACAATCACGGA | 20 |
| OLTBR | GATATAGTCGACTTAATTTTTCATTGAGATAGCAGCGATAGAG | 21 |

OLTB-T1 to OLTB-T6 were used as template primers while OLTBF and OLTBR were used as amplification primers. OEPCR was used for massively amplifying the LT-B gene of preferred codon usage. The PCR mixture (50 μL) comprised 1×GDP-HiFi PCR buffer B, 200 μM of dNTP (dATP, dTTP, dGTP, and dCTP), 1 μM of primer, and 1 U GDP-HiFi DNA polymerase. The PCR condition was one cycle of 98° C. for 2 minutes, 35 cycles of 94° C. for 30 seconds, 55° C. for 30 seconds, and 68° C. for 30 seconds, one cycle of 68° C. for 5 minutes. After the PCR reaction, the PCR product was checked by electrophoresis to see if there was any DNA fragment of expected size. Then a PCR-M™ Clean Up system kit (GeneMark, Taiwan) was used for collecting the PCR product in the gel. Afterwards, the collected PCR product was cut by BamHI and SalI and, the resulting DNA fragment was ligated into pMV6OSPT cut by the same restriction enzymes. The resulting ligation product was transformed into *Escherichia coli* ECOS 9-5. Colony PCR was conducted to screen strains of success transformation; wherein DNA electrophoresis was conducted to confirm the recombinant plasmid did have the insert DNA. Then the plasmid was isolated for DNA sequencing. The plasmid confirmed to have the correct insert DNA via DNA sequencing was named pMV6OSP-OLTBT. Likewise, pMROSP was also modified. The steps were not repeated herein.

Please see FIG. 1, which shows the plasmid pMV6OSP-OLTBT constructed by the present invention. According to the figure, pMV6OSP-OLTBT comprises an expression element (1) (veg6-lacO), a signal peptide (2) (SacBSP), multiple restriction enzyme cutting sites (3), a transcription terminator (4), a selection marker (5) (Ap$^r$: Ampicillin-resistance gene; Tc$^r$: tetracycline-resistance gene), an origin of replication (6) (ex. the origin of replication, ori-177, from *E. coli* plasmid pACYC177, which enables the plasmid to be replicated in *E. coli*; the origin of replication, ori-pAMα1, from *Enterococcus faecalis* DS-5 plasmid pAMα1, which enables the plasmid to be replicated in *Bacillus subtilis*), and a LT-B gene of preferred codon usage (7).

6. Transformation of *Bacillus subtilis*:

Transformation process was conducted in this experiment for transforming the present plasmid into *Bacillus subtilis*. First of all, a *Bacillus subtilis* strain WB800 (having plasmid pBL1, that is a plasmid contributing lad gene expression) was inoculated in a LB medium containing erythromycin (5 μg/mL) and cultured at 37° C. and 150 rpm of shaking overnight. Then, the broth was inoculated into a minimal medium containing 1% of threonine at 1:10 ratio and cultured at 37° C. and 200 rpm of shaking. The culture was continuous until the $OD_{600}$ thereof achieved about 1.0. Then, the broth was centrifugated to collect the pellet. The pellet was washed twice with cold and sterile deionized water, re-suspended in a cold and sterile SHMPYT buffer (0.25 M sucrose, 1 mM Hepes, 1 mM $MgCl_2$, 20% (v/v) polyethylene glycol 6000 (PEG6000), 0.125% tryptone), and dispensed into tubes (100 μL/tube). The cells contained in those tubes were competent cells required for the subsequent experiments. For the DNA transformation experiments, the competent cells were first stored at −70° C. and thawed for use. 100 μL of competent cells were added with 1 μL of the present plasmid and transferred to a pre-chilled cuvette. After the cuvette was chilled for 5 minutes, electroporation was conducted at conditions of 8.75 kV/cm, 500 Ω, 25 μF. The transformed cells were transferred into 1 mL SB medium (3.5% tryptone, 2% yeast extract, 0.5% NaCl, pH 7.0) and cultured at 37° C. and 150 rpm of shaking for 3 hours. Afterwards, a proper amount of broth was plated on a solid medium containing erythromycin (5 μg/mL) and tetracycline (12.5 μg/mL) and cultured at 30° C. for 24 hours.

7. Expression and Detection of Recombinant Protein:

The transformed *Bacillus subtilis* strain was inoculated in a LB medium containing erythromycin (5 μg/mL) and tetracycline (12.5 μg/mL) and cultured at 30° C. and 180 rpm of shaking for overnight. A proper amount of broth was transferred into a fresh LB medium or SR medium both containing erythromycin (5 μg/mL) and tetracycline (12.5 μg/mL) or SR medium containing various concentration of glucose. The sub-culture was initiated at $OD_{600}$ 0.1 and continued at 30° C. and 180 rpm of shaking until $OD_{600}$ 0.5. Then, 1 mM of isopropyl-3-D-thiogalactoside (IPTG) was added for inducing protein expression. At various culture time, a proper amount of broth was collected for centrifugation (10,000×g, 10 minutes). The supernatant was collected for Tricine-SDS PAGE protein electrophoresis. The Tricine-SDS PAGE protein electrophoresis was conducted and modified in accordance Schagger and von Jagow's teaching in 1987. First of all, polyacrylamide gel was prepared. The polyacrylamide gel consisted of three layers of gel, which were respectively stacking gel (4% T, 3% C), spacer gel (10% T, 3% C) and separation gel (16.5% T, 3% C). The gel for electrophoresis was put into an electrophoresis device (ATTO, Japan). Anode buffer (0.2 M Tris, pH 8.9) and cathode buffer (0.1 M Tris, 0.1 M tricine, 0.1% SDS, pH 8.25) were introduced. After the samples were loaded into the sample wells, the electrophoresis was conducted at 80V for 60 minutes and then at 145V for another 80 minutes. Afterwards, the gel was removed from the device and fixed with fixing buffer (50% methanol, 10% acetic acid) for 30 minutes. Then, the fixing buffer was discarded and BLUE BANDIT™ PROTEIN STAIN (Amresco, USA) was added for staining the protein.

Figure 6:
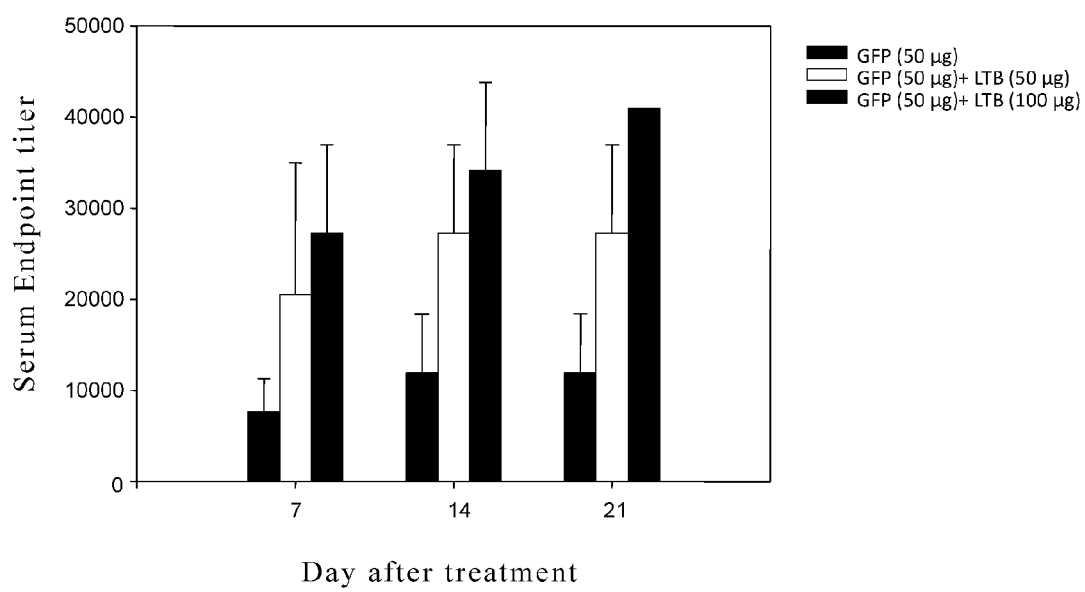

The experiment results were shown in FIG. 2. Lane 1 was the *Bacillus subtilis* strain transformed with pBL1 and pMCST (this strain would not express LT-B; as negative control group). Lane 2 was the *Bacillus subtilis* strain transformed with pBL1 and pMROSP-LTBT of the present invention. Lane 3 was the *Bacillus subtilis* strain transformed with pBL1 and pMV6OSP-LTBT of the present invention. According to the results, the pMV6OSP-LTBT of the present invention displayed higher production.

FIG. 3 shows the change of the LT-B production upon various medium (LB medium or SR medium) and different culture time (24 hours or 48 hours). The data of the figure shows that SR medium may provide higher production. In addition, generally speaking, the longer the culture time, the higher the production. Moreover, in comparison between the data of the *Bacillus subtilis* strain having pBL1 and pMV6OSP-OLTBT and the *Bacillus subtilis* strain having pBL1 and pMV6OSP-LTBT, the modification of the preferred codon usage made to the *Bacillus subtilis* strain did significantly improve the production.

FIG. 4 shows the change of the LT-B production upon culturing in various concentration of glucose. Column 1 of the figure shows the results of the SR medium culture having 0.1 wt % of glucose and 72 hours of induction. Column 2 of the figure shows the results of the SR medium culture having 0.2 wt % of glucose and 72 hours of induction. Column 3 of the figure shows the results of the SR medium culture having 0.4 wt % of glucose and 72 hours of induction. Column 4 of the figure shows the results of the SR medium culture having 0.6 wt % of glucose and 72 hours of induction. According to the results, the SR culture having 0.1 wt % provided the highest production, which was nearly 116 mg/L.

8. Purification of Recombinant LT-B:

Be taking the advantage of LT-B's property in binding with galactose, an immobilized galactose resin (Pierce, USA) was adopted for protein purification. The protein purification in this experiment was conducted by following the operation manual provided by the manufacturer and modified. The culture supernatant of the *Bacillus subtilis* strain was collected for centrifugation (10,000×g, 30 minutes). The supernatant was collected and introduced into a column containing 1 mL of immobilized galactose resin for binding the LT-B therein onto the resin. Then, 30 mL of HEPES buffer was added to wash the resin for washing off the nonspecific-binding proteins or other impurities. The $OD_{280}$ value of the effluent was detected. When the $OD_{280}$ value became stable, the nonspecific-binding proteins shall have been washed off. Last, 10 mL of elution buffer (0.1 M HEPES, 0.15 M NaCl, 0.1 M D-galactose, pH 7.2) was added to elute the LT-B absorbed on resin. The principle of this step was to form an absorption competition between D-galactose of high concentration and the resin to LT-B, thereby causing LT-B be eluted from the resin. A protein electrophoresis was conducted to evaluate the purification of the recombinant LT-B. According to the results shown in FIG. 5, the purity of the purified LT-B achieved at least 95%.

Example 3: The Evaluation of the Adjuvant Effect of the LT-B Prepared by the Present Expression System Enhanced Green Fluorescent Protein (GFP+) was used as model antigen in this experiment for mixing with the present LT-B as adjuvant. The mice used in this experiment were 5-weeks-old BALB/c female mice (purchased from National Laboratory Animal Center, NLAC). The mice were fed with clean food and water in standard animal room with air condition for 7 days before starting the immune tests.

The mice were separated into A, B, C groups. Each group had three mice. Group A was treated with 0.5 mL GFP+ solution (containing 50 μg GFP+, 10 mM $Na_2HPO_4$, and 1.5 mM $NaH_2PO_4$, pH 7.5) via intraperitoneal injection. Group B was treated with 0.5 mL solution containing GFP+ and recombinant LT-B (containing 50 μg GFP+, 50 μg LT-B, 10 mM $Na_2HPO_4$, and 1.5 mM $NaH_2PO_4$, pH 7.5) via intraperitoneal injection. Group C was treated with 0.5 mL solution containing GFP+ and recombinant LT-B (containing 50 μg GFP+, 100 μg LT-B, 10 mM $Na_2HPO_4$, and 1.5 mM $NaH_2PO_4$, pH 7.5) via intraperitoneal injection. Each mouse was treated twice at a 2-week interval Serum samples were collected at the $7^{th}$, $14^{th}$, $21^{st}$ day after the immunization was completed. An ELISA assay was conducted to determine the titer of the anti-GFP+ IgG immunoglobulin and the adjuvant effect of the present LT-B. The results are shown in FIG. 6. The results show that the more the amount of LT-B added, the higher the titer of the anti-GFP+ IgG immunoglobulin. In other words, the present LT-B does effectively improve the immunogenicity.

Those having ordinary skill in the art can readily understand any possible modifications based on the disclosure of the present invention without apart from the spirit of the present invention. Therefore, the examples above shall not be used for limiting the present invention but intend to cover any possible modifications under the spirit and scope of the present invention according to the claims recited hereinafter.

What is claimed is:

1. A plasmid for producing *Escherichia coli* heat labile enterotoxin B-subunit, comprising:

a nucleotide sequence encoding *Escherichia coli* heat labile enterotoxin B-subunit; and an expression element recognizable by *Bacillus subtilis;* wherein said expression element is rpsJ-lacO expression element, veg6-lacO expression element, or a combination thereof.

2. The plasmid of claim 1, wherein said nucleotide sequence encoding *Escherichia coli* heat labile enterotoxin B-subunit has a sequence of SEQ ID NO: 01.

3. The plasmid of claim 1, wherein said *Escherichia coli* heat labile enterotoxin B-subunit has an amino acid sequence of SEQ ID NO: 02.

4. The plasmid of claim 1, wherein said expression element recognizable by *Bacillus subtilis* is rpsJ-lacO expression element, and wherein said rpsJ-lacO expression element has a nucleotide sequence of SEQ ID NO: 03.

5. The plasmid of claim 1, wherein said expression element recognizable by *Bacillus subtilis* is veg6-lacO expression element, and wherein said veg6-lacO expression element has a nucleotide sequence of SEQ ID NO: 04.

6. The plasmid of claim 1, further comprising a nucleotide sequence encoding a signal peptide of a secretory protein.

7. The plasmid of claim 6, wherein said signal peptide is a signal peptide of levansucrase.

8. The plasmid of claim 7, wherein said signal peptide of levansucrase has a nucleotide sequence of SEQ ID NO: 05.

9. A method for producing *Escherichia coli* heat labile enterotoxin B-subunit, comprising expressing said plasmid of claim 1 in a *Bacillus subtilis* expression system.

10. The method of claim 9, wherein said nucleotide sequence encoding *Escherichia coli* heat labile enterotoxin B-subunit of said plasmid has a sequence of SEQ ID NO: 01.

11. The method of claim 9, wherein said plasmid further comprises a nucleotide sequence encoding a signal peptide of a secretory protein.

12. The method of claim 11, comprising the following steps:

(A) culturing a strain of *Bacillus subtilis* transformed with said plasmid in a culture medium;

(B) inducing the expression of said nucleotide sequence encoding *Escherichia coli* heat labile exterotoxin B-subunit of said plasmid; and (C) collecting said culture medium and obtaining said *Escherichia coli* heat labile enterotoxin B-subunit via purification.

13. The method of claim 12, wherein said culture medium is LB medium, SR medium, or a combination thereof.

14. The method of claim 12, wherein said strain of *Bacillus subtilis* expresses LacI, and said expression element recognizable by *Bacillus subtilis* of said plasmid is rpsJ-lacO expression element or veg6-lacO expression element; said inducing of said step (B) is achieved by adding allolactose or isopropyl β-D-thiogalactopyranoside.

15. The method of claim 12, wherein said step (B) is not conducted until said culturing of said step (A) achieves an $OD_{600}$ of 0.3 to 0.5.

16. The method of claim 12, wherein said purification is achieved by introducing said culture medium through an immobilized galactose resin column.

17. The method of claim 12, wherein a production of said *Escherichia coli* heat labile enterotoxin B-subunit is 100 mg/L to 200 mg/L based on a total volume of said culture medium of said step (C).

18. The method of claim 12, wherein said culturing of said step (A) is continuous for 24 to 72 hours.

19. The method of claim 12, wherein said culture of said step (A) contains 0.1 wt % to 0.8 wt % of glucose based on a total weight of said culture medium of said step (A).

20. A kit for producing *Escherichia coli* heat labile enterotoxin B-subunit, comprising:

a strain of *Bacillus subtilis* transformed with said plasmid of claim 1.

21. The kit of claim 20, wherein said *Bacillus subtilis* expresses LacI.

22. The kit of claim 21, further comprising a reagent for inducing the expression of said plasmid, wherein said reagent is allolactose or isopropyl β-D-thiogalactopyranoside.

* * * * *